United States Patent
Ray et al.

(10) Patent No.: US 10,136,870 B2
(45) Date of Patent: Nov. 27, 2018

(54) EXTREMITY IMAGING FOR ANIMALS

(71) Applicant: Carestream Health, Inc., Rochester, NY (US)

(72) Inventors: Lawrence A. Ray, Rochester, NY (US); Edward B. Gindele, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 288 days.

(21) Appl. No.: 14/979,675

(22) Filed: Dec. 28, 2015

(65) Prior Publication Data

US 2016/0361036 A1    Dec. 15, 2016

Related U.S. Application Data

(60) Provisional application No. 62/174,010, filed on Jun. 11, 2015.

(51) Int. Cl.
*A61B 6/03* (2006.01)
*A61D 3/00* (2006.01)
(Continued)

(52) U.S. Cl.
CPC .............. *A61B 6/508* (2013.01); *A61B 6/035* (2013.01); *A61B 6/4435* (2013.01); *A61B 6/589* (2013.01);
(Continued)

(58) Field of Classification Search
CPC .... A61B 6/00; A61B 6/02; A61B 6/03; A61B 6/032; A61B 6/035; A61B 6/04; A61B 6/10; A61B 6/102; A61B 6/107; A61B 6/44; A61B 6/4411; A61B 6/4429; A61B 6/4435; A61B 6/4447; A61B 6/4458; A61B 6/4464; A61B 6/508; A61B 6/547; A61B 6/58; A61B 6/589; A61N 5/10; A61N 5/1048; A61N 5/1049; A61N 5/1056; A61N 5/1059; A61N 5/1077; A61N 5/1081; A61N 5/1083; A61N 5/1092; A61N 5/1094; G05B 2219/40; G05B 2219/40293; G05B 2219/40296; A61D 3/00; A61D 99/00;
(Continued)

(56) References Cited

U.S. PATENT DOCUMENTS

| 4,894,855 A | * | 1/1990 | Kresse | A61B 6/032 |
| | | | | 378/189 |
| 6,155,713 A | * | 12/2000 | Watanabe | A61B 6/4441 |
| | | | | 378/197 |

(Continued)

FOREIGN PATENT DOCUMENTS

| GB | 2 028 053 | 2/1980 |
| JP | 2000-210280 | 8/2000 |
| WO | WO 2010/044844 | 4/2010 |

OTHER PUBLICATIONS

International Search Report dated Feb. 2, 2015 for International Application No. PCT/US2014/059850, 2 pages.

*Primary Examiner* — Anastasia Midkiff

(57) ABSTRACT

An apparatus captures radiographic images of an animal standing proximate the apparatus. A moveable x-ray source and a digital radiographic detector are hidden from view of the animal and are revolved about a portion of the animal's body to capture one or a sequence of radiographic images of the animal's body.

20 Claims, 11 Drawing Sheets

(51) Int. Cl.
*H05G 1/04* (2006.01)
*A61B 6/00* (2006.01)
*A01K 29/00* (2006.01)
*A61B 6/04* (2006.01)
*A61B 6/02* (2006.01)
*A61B 6/10* (2006.01)

(52) U.S. Cl.
CPC .............. *A01K 29/005* (2013.01); *A61B 6/027* (2013.01); *A61B 6/032* (2013.01); *A61B 6/04* (2013.01); *A61B 6/102* (2013.01); *A61B 6/4007* (2013.01); *A61B 6/4085* (2013.01); *A61B 6/4233* (2013.01); *A61B 6/5205* (2013.01); *A61D 2003/006* (2013.01); *H05G 1/04* (2013.01)

(58) Field of Classification Search
CPC ...... A61D 2003/006; H05G 1/00; H05G 1/02; H05G 1/04; A47B 13/00; A01K 29/005
See application file for complete search history.

(56) References Cited

U.S. PATENT DOCUMENTS

| | | | |
|---|---|---|---|
| 6,200,024 B1* | 3/2001 | Negrelli | A61B 6/4233 378/196 |
| 6,496,558 B2* | 12/2002 | Graumann | A61B 6/0478 378/197 |
| 2008/0056451 A1* | 3/2008 | Gotoh | A61B 6/4441 378/197 |
| 2009/0185663 A1* | 7/2009 | Gaines, Jr. | A61B 6/0457 378/209 |
| 2010/0278300 A1 | 11/2010 | Yorkston et al. | |
| 2011/0228901 A1 | 9/2011 | Yorkston et al. | |
| 2012/0014503 A1* | 1/2012 | Ullberg | A61B 6/032 378/19 |
| 2013/0089179 A1* | 4/2013 | Kenny | A61B 6/04 378/62 |
| 2014/0177799 A1* | 6/2014 | Noda | G01N 23/04 378/62 |
| 2015/0004558 A1* | 1/2015 | Inglese | A61B 6/14 433/29 |
| 2015/0313557 A1* | 11/2015 | Mackie | A61B 6/04 378/14 |

* cited by examiner

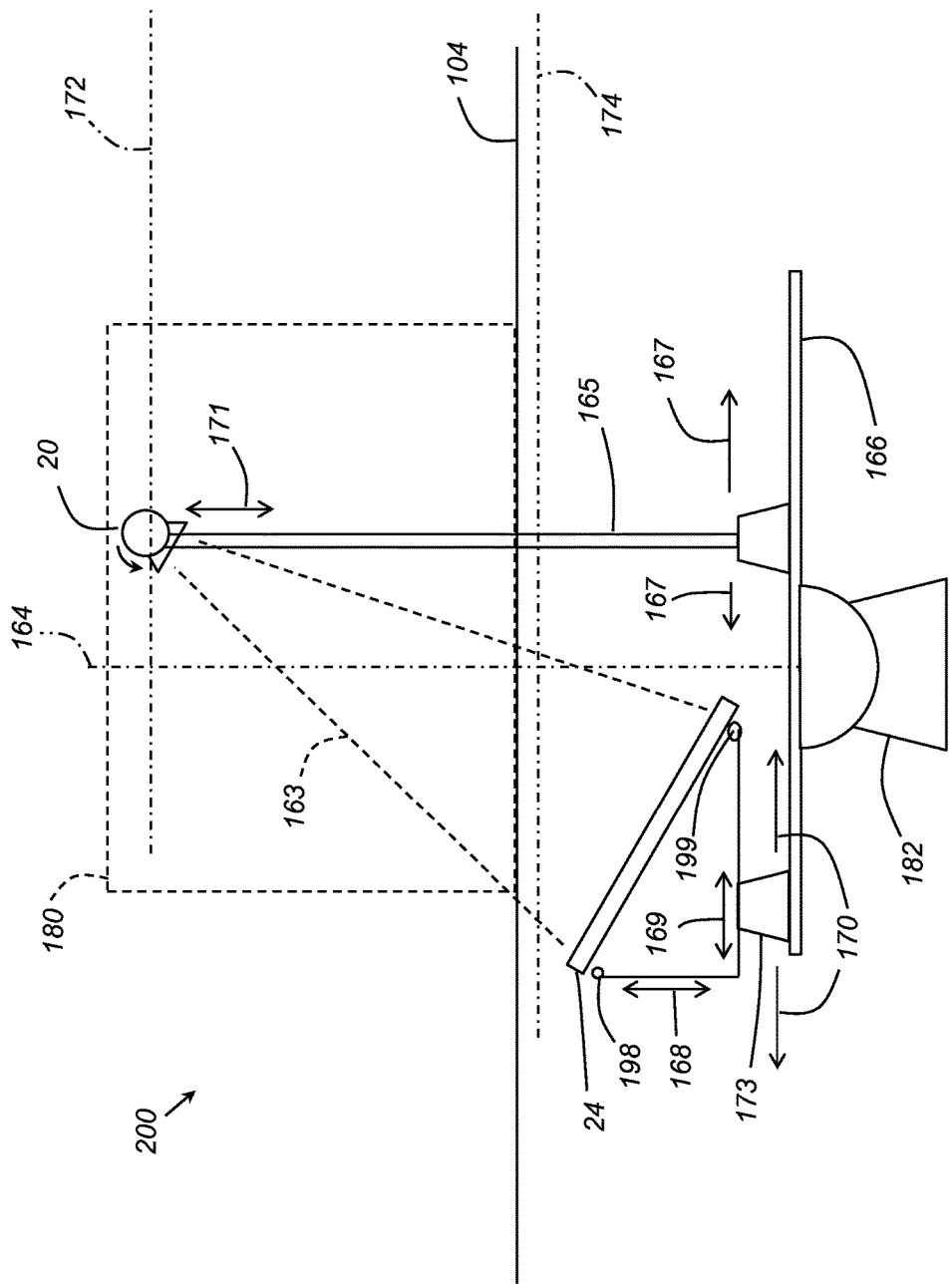

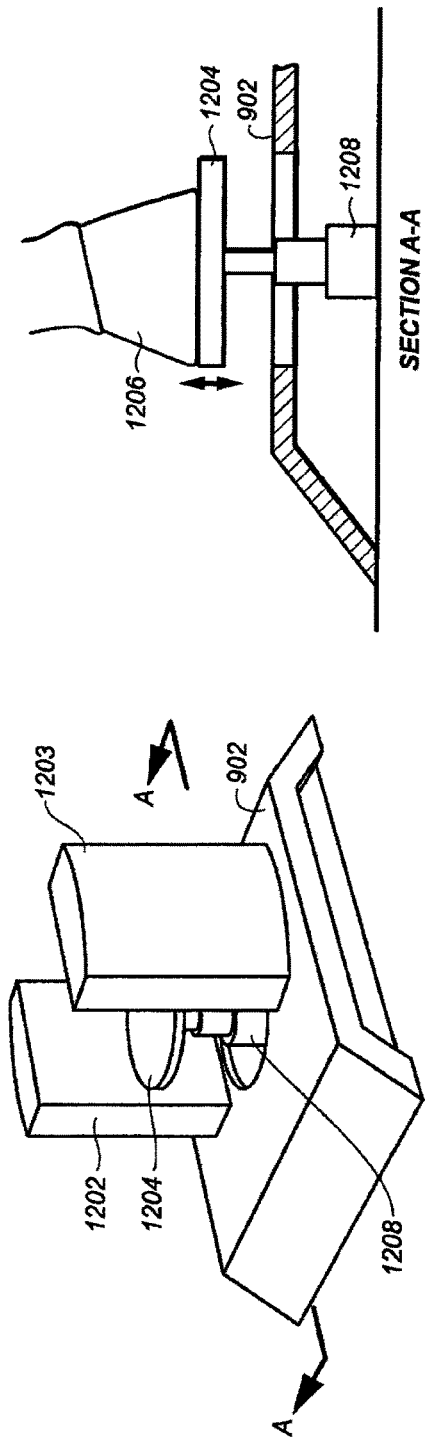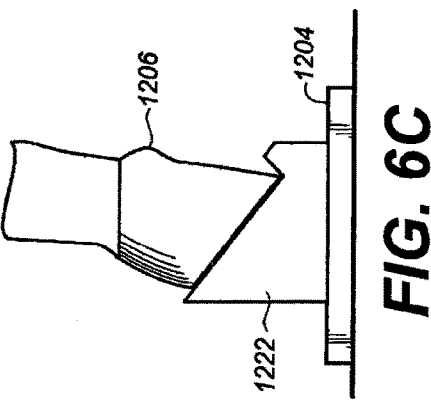
FIG. 6A  FIG. 6B  FIG. 6C

EXTREMITY IMAGING FOR ANIMALS

CROSS REFERENCE TO RELATED APPLICATIONS

This application claims priority to U.S. Patent Application Ser. No. 62/174,010, filed Jun. 11, 2015, in the name of Ray et al., and entitled EXTREMITY IMAGING FOR ANIMALS.

BACKGROUND OF THE INVENTION

The subject matter disclosed herein relates to radiographic imaging of standing subjects, in particular, to applications using Cone-Beam Computed Tomography imaging.

Cone-Beam Computed Tomography (CBCT) imaging would provide a useful tool for diagnosis and treatment assessment, planning, and tracking for an animal as the imaging subject. Certain exemplary CBCT imaging apparatus and methods described herein may address a number of practical challenges for performing CBCT imaging in veterinary applications that relate to considerations such as protection and cleaning of the equipment, shielding of technicians and practitioners during imaging, humane treatment of the animal subject in positioning and restraining the subject for imaging, and efficient use of imaging time and resources. Imaging apparatus embodiments may include a number of features for helping to guide the animal into position and keep the animal in position during imaging. Other considerations may include animal response and behavior in preparing for imaging, during an imaging scan, and afterward, with the expectation that animal behavior may be unpredictable.

Animals have a fright-flight response to circumstances that are unfamiliar. Consequently, when a large animal attempts to escape the surroundings there is a significant potential for equipment damage and more importantly physical injury to the animal. A means to minimize the potential for damage and injury is for minimize the physical access of the CBCT system components. Equipment damage to the detector can result in detector replacement costs that constitute a significant portion of the cost of the CBCT system. The cost for injury to an animal is incalculable due to the uncertainty of the scope of potential injury.

A typical configuration for a CBCT system is for the detector and the source to orbit the object of interest such that the detector is parallel to the axis-of-rotation and the center of the detector is in the same plane as the orbit of the source. The object of interest is positioned at or near the axis of rotation of the system and the reconstructed object is centered on the orbital plane of the source. In this configuration the detector and source need to straddle the animal's leg. In the situation where the animal attempts to flee there may be parts of the imaging system that could easily be damaged by the animal or injure the animal. The present invention is a means to address this problem.

The discussion above is merely provided for general background information and is not intended to be used as an aid in determining the scope of the claimed subject matter.

BRIEF DESCRIPTION OF THE INVENTION

A cone-beam-computed-tomography (CBCT) system for large animals, such as equines and bovines, which does not require full sedation thereof is highly desirable. However, equines are finicky animals and tend to react erratically in situations that they are uncomfortable. A CBCT system consists of two major components, a source and a detector, where both are moved about the object of interest. The normal configuration is for the detector and the source to be oriented on opposite sides of an axis of rotation such that a straight line between the two is orthogonal to the axis of rotation. The two components are normally rotated about the axis of rotation by what is termed 180 degrees plus fan angle. For instance, a common range is 210 degree rotation. This implies during the data capture phase, either the detector or the source traverses every position on a circle. Two problems arise from such a configuration. The first is that either the detector or the source is in the position liable to receive a kick, and subsequent damage to the CBCT, from the animal if it is startled. Second if the animal decides to flee, then the components would be in likely path of the animal resulting in possible damage to the equipment or injury to the animal.

To minimize these problems a novel configuration for the components is envisioned. The source will be positioned such that its orbit, or path, presents the least chance of being kicked or being in the path the animal is likely to take if it decides to flee, as well as being configured to enable the animal to be comfortably positioned in the system. In one embodiment, the source and detector orbit planes are parallel but offset by some distance that is determined prior to the examination imaging series.

The detector may be placed in a track under the animal in such a manner that there is absolutely no possibility for the animal to physically interact with the detector. This greatly reduces the chance of equipment damage, and if damage occurs the source will likely be the damaged part. This is significant as the detector is the more expensive component. The configuration of the CBCT system, or CBCT stall will be described herein.

In one embodiment, as the animal is placed in the CBCT stall, the source is raised to a desired height and its angle is tilted to the meet with a preferred location of the detector, e.g., the center, and optionally, the detector is tilted to be closer to orthogonal to a central ray of the x-ray beam. During the data capture phase the detector and source move in parallel orbital planes about the central axis.

The detector may be placed in a race below the floor of the imaging system so that the animal never has an opportunity to physically access the detector. Consequently, the animal can be brought into the CBCT-stall and allowed to walk over the detector until it is suitably positioned. This also has the advantage in that the animal does not perceive any movement of the device, which could cause the animal to bolt or become startled.

Ideally, for capturing projections for the front legs, the detector is placed in front of the animal to begin a scan sequence, and for the rear legs the detector is moved to be parallel to the animal to begin a scan sequence. Of course, it is also possible to have the detector assembly be placed parallel or front wise to the animal in either case. If a series for capturing the animal's head is desired, the then animal can be brought down so its nose is placed near the axis of rotation, but above the floor. Again the detector and source are tilted to provide a suitable coverage of the animal's head.

Having the detector in a race below the floor also permits the detector to be moved in a radial direction prior to the scan to enable imaging of the hooves or other anatomy of the animal that is closer to the floor. The configuration of the source and detector can also move along paths that are more exotic to examine the physiology of a horse, for example.

For instance it may be beneficial to move the detector in a path that at some points is closer to the axis of rotation, such as a curved or elliptical path.

The initial placement of the detector and source need to be sensed and reported in order to perform any subsequent reconstruction algorithm. This can be accomplished with multiple methods. The information needed includes the starting rotation angles, the height of the source, the declination angle of the source, the radial position of the detector, the tilt angle of the detector, the number of projection images captured and the angle between successive projections. An overall control system to coordinate the imaging system is standard in any CBCT system. The reconstruction of the 3D volume from the projection images can be performed using a standard algebraic reconstruction method. However, modifying the algorithm to account for specific aspects of a customized configuration is possible.

In one embodiment, the system eliminates a major component of the system from restricting the movement of the animal either in positioning the animal or in case the animal moves unexpectedly. This reduces the chance of injury to the animal and damage to the equipment. Although several examples disclosed herein depict an exemplary subject animal as a horse, the disclosed embodiments may be used for a variety of animals. For example, bovine imaging may be useful at a dairy farm to monitor health of cows' hooves. Other large and smaller animals may be safely radiographically imaged such as at a zoo, for example.

Exemplary extremity imaging apparatus embodiments described herein may alternately be used for tomography imaging over a narrower range of angles than is sometimes used for CBCT imaging, for fluoroscopy, or for single-image radiography applications. It may be useful, for example, to obtain a number of radiography images of the same subject animal exposed at different angles. Images may be obtained by directing radiation through the subject animal at successive angular positions and capturing an image at each angular position. The image acquisition system may include a source of radiographic (x-ray) energy, a digital radiography (DR) detector, and related components that support orbiting of the source and detector over the range of desired angles, so that the source and detector may be substantially 180 degrees apart during the orbit, with the subject between them at every imaging position. The anatomical region of the subject animal may include a single extremity, such as a leg or head. Alternatively, a pair of legs or other features may be simultaneously imaged. The apparatus disclosed herein captures radiographic images of an animal standing on the apparatus. The base of the apparatus is a platform for the animal to stand upon, although components of the apparatus may also be constructed beneath an existing floor. Additionally, under the platform, or floor, a detector, a track for the detector, a means to move the detector along a detector path, a means to modify the vertical position of the detector and, alternatively, a means to modify the detector path diameter, is disclosed.

The apparatus includes a moveable x-ray source that is attached to the system, though above the detector assembly. The source has the ability to make exposures at a rate and dose adequate for CBCT applications; for instance at 20 exposures per second. The source is also synchronized with the detector so both subsystems move in parallel orbital planes about the axis-of-rotation and with the positions within their respective orbits being approximately 180 degrees apart. The x-ray source also can be positioned in order that its location is not in the immediate physical proximity to the animal, or is not visible to the animal. This also reduces the potential for damage or injury in case the animal attempts to flee. An advantage that may be realized in the practice of some disclosed embodiments of the imaging system is convenient and portable radiographic imaging of animals at remote sites.

In one embodiment, an apparatus for radiographic imaging of an animal is disclosed. The apparatus comprises a support base to support the animal while standing on its legs. A moveable x-ray source is disposed within a source housing and is mechanically attached to a rotational orbital mechanism. A digital radiographic detector may also be mechanically attached to the same rotational orbital mechanism, or a different rotational mechanism configured to rotate simultaneously with the source rotational mechanism. The source housing may extend upward substantially perpendicular to, and above, a top surface of the support base or floor, and is configured to capture a radiographic image of an extremity, such as the leg, or other anatomy of the animal.

In one embodiment, an apparatus for radiographic imaging of an animal includes a surface to support an animal standing on its legs. A moveable x-ray source is disposed above the surface within a source housing and is mechanically revolved. A digital radiographic detector is disposed below the surface and is rotated in a position diametrically opposed to the source. The source housing remains stationary and the x-ray source and the detector are configured to revolve around at least one of the limbs of the animal to capture at least one radiographic image thereof.

In one embodiment, an apparatus for radiographic imaging comprises a support surface to support a subject, an x-ray source facing one side of the support surface, and a digital radiographic detector facing a second side of the support surface and operating cooperatively with the x-ray source to capture one or more radiographic images of the target.

Once the images are collected, a process, known as reconstruction, takes the images and produces a volumetric estimation of the object. There are numerous reconstruction algorithms, however many of these methods assume a particular geometric configuration of the source, object and detector. Since the detector orbit is not in the same plane as the source, and moreover the detector has an angle which is not orthogonal to the detector orbital axis, reconstruction algorithms are required to account for this geometric arrangement. It is preferred that a so-called algebraic reconstruction method be utilized. These are generically referred to as ART methods, and there are numerous variations of this method, such as sequential ART, statistical ART, as well as numerous optimization methods to yield results, given specific known properties of the system.

So that the manner in which the features of the invention can be understood, a detailed description of the invention may be had by reference to certain embodiments, some of which are illustrated in the accompanying drawings. For example, the summary descriptions above are not meant to describe individual separate embodiments whose elements are not interchangeable. Many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

It is to be noted that the drawings illustrate only certain embodiments of this invention and are therefore not to be considered limiting of its scope, for the scope of the invention encompasses other equally effective embodiments. The drawings may be not necessarily to scale, emphasis generally being placed upon illustrating the features of certain embodiments of the invention. In the drawings, like numerals may be used to indicate like parts throughout the various views. Thus, for further understanding of the invention, reference can be made to the following detailed description, read in connection with the drawings in which:

FIG. 1C is a diagram of the side view of the imaging system for animals of FIG. 1B showing adjustable features;

FIG. 6A is a perspective view of an embodiment of a pedestal for positioning a foot of an animal to be imaged;

FIG. 6B is a cross-sectional view along section A-A of the pedestal of FIG. 6A for positioning a foot of an animal to be imaged;

FIG. 6C is a side view of an embodiment of an alternative exemplary pedestal for positioning a foot of an animal to be imaged.

DETAILED DESCRIPTION OF THE INVENTION

Figure 1A:
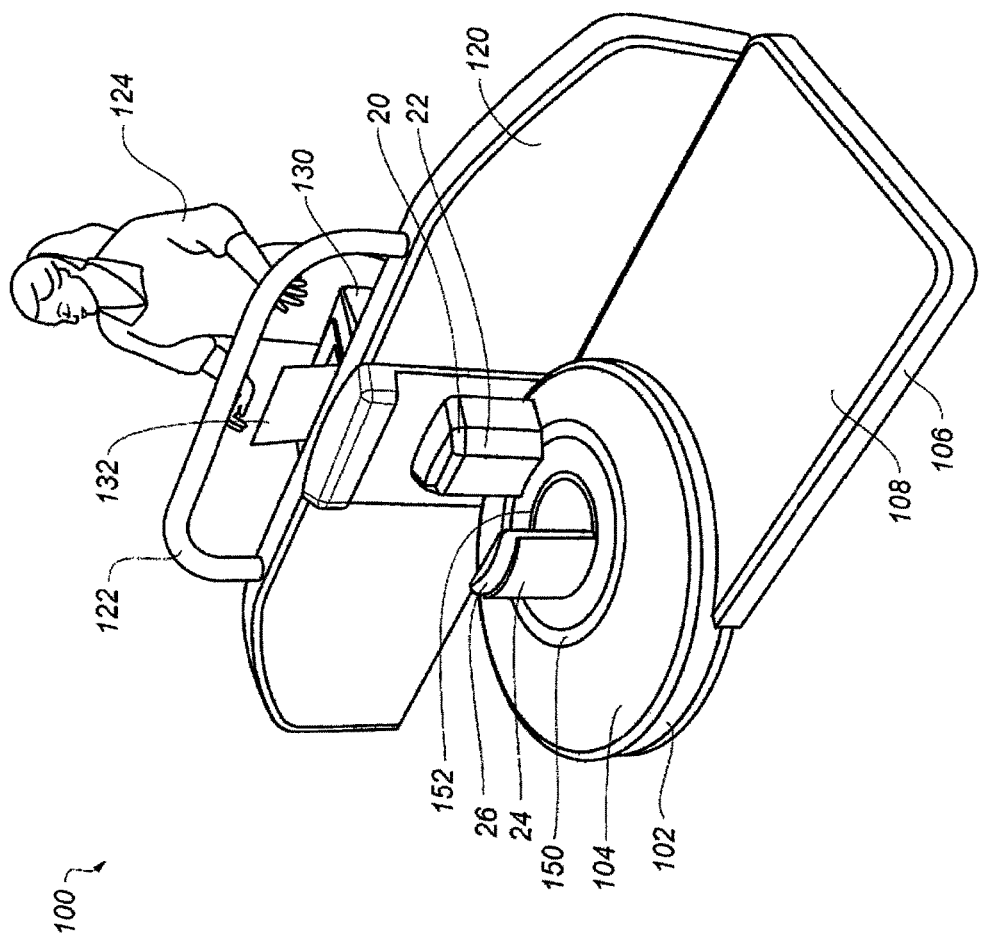
FIG. 1A is a perspective view of one embodiment of an exemplary imaging system for animals.
Figure 1B:
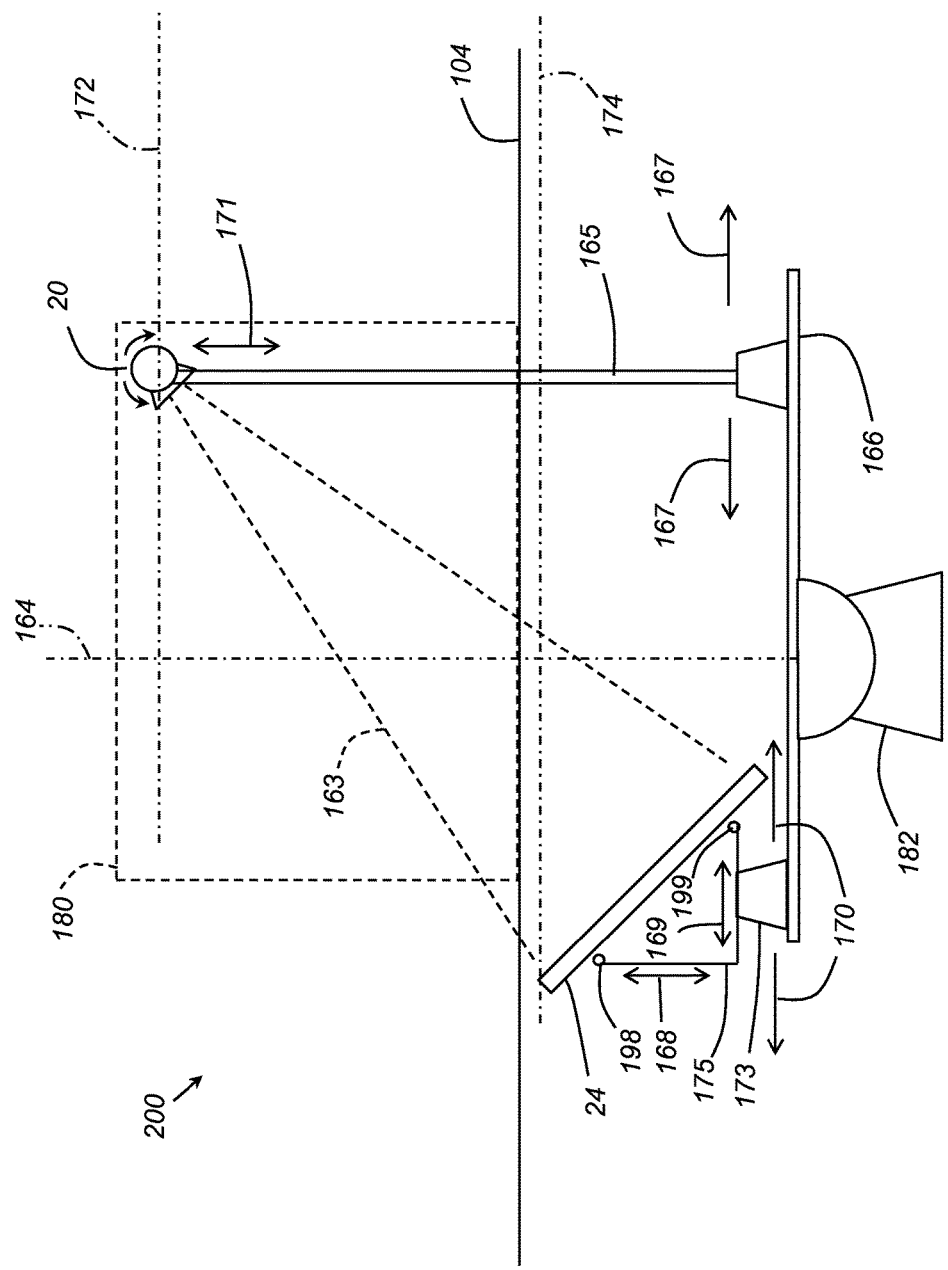
FIG. 1B is a diagram of a side view of a portion of an exemplary imaging system for animals.

It may be helpful to briefly explain a prior art embodiment of an animal imaging system before describing the novel embodiment of the present invention that is illustrated beginning with FIG. 1B. With reference to the prior art embodiment of FIG. 1A, there is illustrated an embodiment of an exemplary radiographic extremity imaging system 100. The extremity imaging system 100 may include a substantially circular support base 102 having a generally planar top surface 104 to provide a platform for supporting a subject animal, such as its forelegs, hind legs, or both. The support base 102 may be configured to be rotatable about a central axis through the center of the support base 102, as described herein. Attached to the support base 102 may be a platform 106 having a generally planar top surface 108 to support an animal to be imaged, such as its forelegs or hind legs. The platform 106 may be movable about the perimeter of the support base 102 to assist in positioning a subject animal for ease of imaging access to separate limbs of the animal. The top surface 108 of the platform 106 may be lower than the top surface 104 of the support base 102, as shown, or it may be at the same height or higher than the top surface 104 of the support base 102, depending on the desired level of the platform 106. The top surfaces 104, 108 may include a slip-resistant rubber mat or other suitable padding, hard surface, or cushioning for supporting an animal. The support base 102 base may be sized to support all four legs of a horse, for example, or only the forelegs or hind legs thereof. The support base 102 may have an adaptable arrangement of slots, mounting blocks, or other fittings to support permanent or removable structures that may help to guide the animal and help to shield equipment and personnel from animal movement, such as from kicking or stomping. The support base 102, as well as the platform 106 may include various shapes such as, but not limited to, the rounded design as shown in FIG. 1A, as well as rectangular shapes described herein. The support base 102 may also contain or support an x-ray imaging detector, an x-ray source, or a combination thereof, and other devices to permit a range of imaging configurations. An x-ray imaging detector and an x-ray source may be attached to any of the support platforms, or configured to be rotated in relation to a position of an animal standing on the support surfaces 104, 108, and other devices to permit a range of imaging configurations, as described herein.

The extremity imaging system 100 may include a wall 120 which may include a radio-opaque material to provide a protective radiation shield for personnel or other animals near the imaging system 100 from radiographic energy emanating therefrom. The wall 120 may extend along the length of the support base 102 and the platform 106. The wall 120 may further include an attached rail 122 to be used for added support by an animal to be imaged or by an operator 124, such as those who may lead an animal into position for imaging on the extremity imaging system 100. Operative control of the extremity imaging system 100 may be programmed via a connected processing system 130 that includes a display 132, which may be controlled and operated via a user interface for receiving inputs from the operator 124.

The extremity imaging system 100 may include a radiation source 20 within a source housing 22 and a radiation detector 24 within a detector housing 26. For ease of reference, the radiation source 20 and its housing 22 may be referred to herein as the "source" and the radiation detector 24 and its housing 26 may be referred to as the "detector". The source and detector may both be mounted on or above the top surfaces 104, 108, or either of these may be mounted below the top surfaces 104, 108, to an orbital transport apparatus. The orbital transport apparatus may have portions located below the top surfaces 104, 108, such as within the base support 102. The orbital transport apparatus serves to revolve the source and detector about a common central orbital axis that is generally perpendicular to the top surface 104 of the support base 102 whereby the source and detector are both at least partially in a common rotational plane parallel to the top surface 104 during an imaging scan of a subject animal. Depending on the anatomical region of the subject animal being imaged, the forelegs of the animal may be positioned on the support base 102 while the hind legs may be positioned on the platform 104, and vice versa. Such positioning is exemplary only, and such positioning may depend on the size of the animal as well as on the size of the support base 102 and the platform 106. Thus, the orbital transport apparatus may be used to revolve the source and detector at various selectable angles about a limb of a standing animal or other anatomical region of an animal positioned between the source and detector. For the sake of reference terminology, as used herein, the orbital transport mechanism may be said to "rotate" about a central axis which causes the source and detector to "revolve" about the same central axis.

To enable movement of the source or detector above the top surface 104 of the support base 102, the support base 102 may include a moveable circular or curved portion 150 to which the revolving radiation source may be attached. Similarly, the support base may include a moveable circular or curved portion 152 to which the revolving detector may be attached. Alternatively, circular or curved slots or openings may be formed in the top surface 104 to allow movement therethrough by the source or detector via an orbital transport apparatus positioned beneath the top surface 104 within the support base 102, whereby the source or detector is supported by a rigid arm extending through the slot from below the top surface 104. Thus, the elements 150 and 152 referenced in FIG. 1A may represent either moveable portions of the top surface 104, such as ring shaped portions, and they may represent slots through which the source or detector, or both, are attached to, and driven by, an orbital transport apparatus under the top surface 104. Alternatively, the orbital transport apparatus may extend through such slots 150, 152 to secure and support the source or detector, respectively, or both, at about the level of the top surface 104 to revolve the source and detector about a common central orbital axis that is generally perpendicular to the top surface 104 of the support base 102 whereby the source and detector are both at least partially with a common rotational plane parallel to the top surface 104. In one embodiment, the support base 102 may be large enough, with respect to its height, to allow storage of the source and detector within the support base 102 by lowering the source and detector through the slots 150, 152 into the support base 102. The source and detector may then be raised and emerge from below the top surface 104 through slots 150, 152. The source and detector housings may be raised manually, or by use of a motorized actuator, before or after the subject animal is moved into an appropriate position on the base support 102 for imaging.

The orbital transport apparatus may be configured to carry the source about the subject animal's extremity to be imaged. In one embodiment, the orbit may be circular, somewhat non-circular, such as elliptical, or otherwise curved. The orbit of the source generally defines a scan volume, such as a cylindrical scan volume associated with a circular orbit, for the imaging system 100. The orbit may be centered or offset relative to a center of the support base 102. In one embodiment, the offset may be configured in coordination with the source's housing 22. The source may generally orbit about the central orbital axis; its orbital path may be circular so that its radius about the central axis has a fixed value for any CBCT imaging sequence. The central orbital axis may define an ideal position wherein a subject animal's anatomical region, such as a limb, may be positioned for the imaging exposure sequence, although it may be necessary to image an animal positioned offset from the central orbital axis.

Using any of these alternative configurations, the source and detector may each be revolved a full 360 degrees, or may revolve only about 180 degrees plus a cone beam angle as emitted by the source 20, which may determine an arc between about 190 to about 240 degrees for each of the source and detector. Generally, movement of the source corresponds to a simultaneous rotational movement of the detector, thus, both the source and detector may be mounted to a common support structure for simultaneously revolving both during a scanning sequence, for example. Alternatively, the source and detector may be independently moveable to provide an option of adjusting a position of one or both for desired imaging schemes. According to an alternate embodiment of the imaging system 100, the support base 102 may be rotatable in turn-table fashion. The subject animal may be positioned on the support base during rotation and thus also rotates. In one embodiment, the source and detector may remain stationary as the support base rotates during an imaging sequence.

FIG. 1B is a side view diagram of an imaging system 200 in one embodiment of the present invention wherein the detector 24 and the detector path indicated by arrows 192 (FIG. 1D) remain entirely below the top surface 104 (floor) of the support base 102. The detector 24 revolves about the central axis 164 along the detector path in either direction 192 (FIG. 1D) while remaining, at least partially, in a detector path plane 174 that is generally parallel to the top surface 104 of the support base 102. Typically, the source 20 and the detector 24 revolve in a selected one of the directions 191, 192, respectively (FIG. 1D), during an imaging scan. The source 20 remains above the top surface 104 of the support base, or floor. The source 20 and detector 24 revolve about a central axis 164 that may be generally perpendicular to the top surface 104. The source 20 and detector 24 may be attached to a rotating orbital transport mechanism comprising a rigid arm 166, or alternatively a rigid disc 176 (FIG. 1D), which, in turn, is attached to a rotating motor 182 to propel the source and detector about the central axis 164, whereby the source 20 generally revolves about the central axis 164 165 while at least partially remaining in the source plane 172 that is generally parallel to the top surface 104. The source 20 may be rotatably attached to a rigid extension 165 which, in turn, is adjustably attached to the rigid arm 166. Similarly, the detector 24 may be adjustably attached to rigid extension 173, via a bracket (or bucky) 175, which, in turn, is attached to the rigid arm 166. The source 20 may be attached to the rigid extension 165 such as by a hinge so as to be rotatably adjustable to aim its generated x-ray beam 163 toward the detector 24 at various angles, as desired. The top of the rigid extension 165 may include a telescoping portion to raise or lower the source 20, indicated by arrow 171, as desired. The rigid extension 165 may be attached to rigid arm 166 so as to be slidably adjusted and positioned along the rigid arm 166 to move the source 20 nearer or further from the central axis 164, as indicated by arrows 167, as desired. The detector 24 may be attached to the rigid extension 173 such as by a bracket 175 so as to be rotatably adjustable to receive generated x-ray beam 163 from the source at a desired angle, which may be selected such that a central ray of the x-ray beam 163 impacts a central portion of the detector 24 orthogonally. The bracket 175 may include connectors 198, 199 adjustable in vertical direction 168 or horizontal direction 169 to allow the detector 24 to be adjustably positioned at various angles, as desired. In one embodiment, the connectors 198, 199 may be configured to be under motorized and/or programmable control. The bracket 175 may include a bucky used to secure and adjustably position the detector 24 therein. The rigid extension 173 may be attached to rigid arm 166 so as to be slidably adjusted and positioned along the rigid arm 166 to move the detector 24 nearer or further from the central axis 164, indicated by arrows 170, as desired. In one embodiment, a radial distance of the source 20 from the central axis 164 is greater than a radial distance of the detector 24 from the central axis 164. A housing 180 may generally enclose the source and source path, indicated by arrows 191 (FIG. 1D).

FIG. 1C is a side view diagram similar to that shown in FIG. 1B whereby angular and radial positions of the source 20 and detector 24 are adjusted as described herein. The source 20 is moved closer to the central axis 164 by slidably moving the rigid extension 165 closer to the central axis along the rigid arm 166, while the source 20 is tilted downward more sharply. In turn, the detector 24 is tiltably adjusted by lengthening the bracket 175 in the direction 169 and shortening the bracket 175 in the vertical direction 168. The detector may also be moved closer to the central axis 164 along the rigid arm 166 by slidably moving the rigid support 173 toward the central axis 164 along the rigid arm 166 as indicated by arrows 170. In the adjusted position of FIG. 1C a central ray of the x-ray beam 163 emitted by source 20 again impacts a central portion of the detector 24 orthogonally.

Figure 1D:
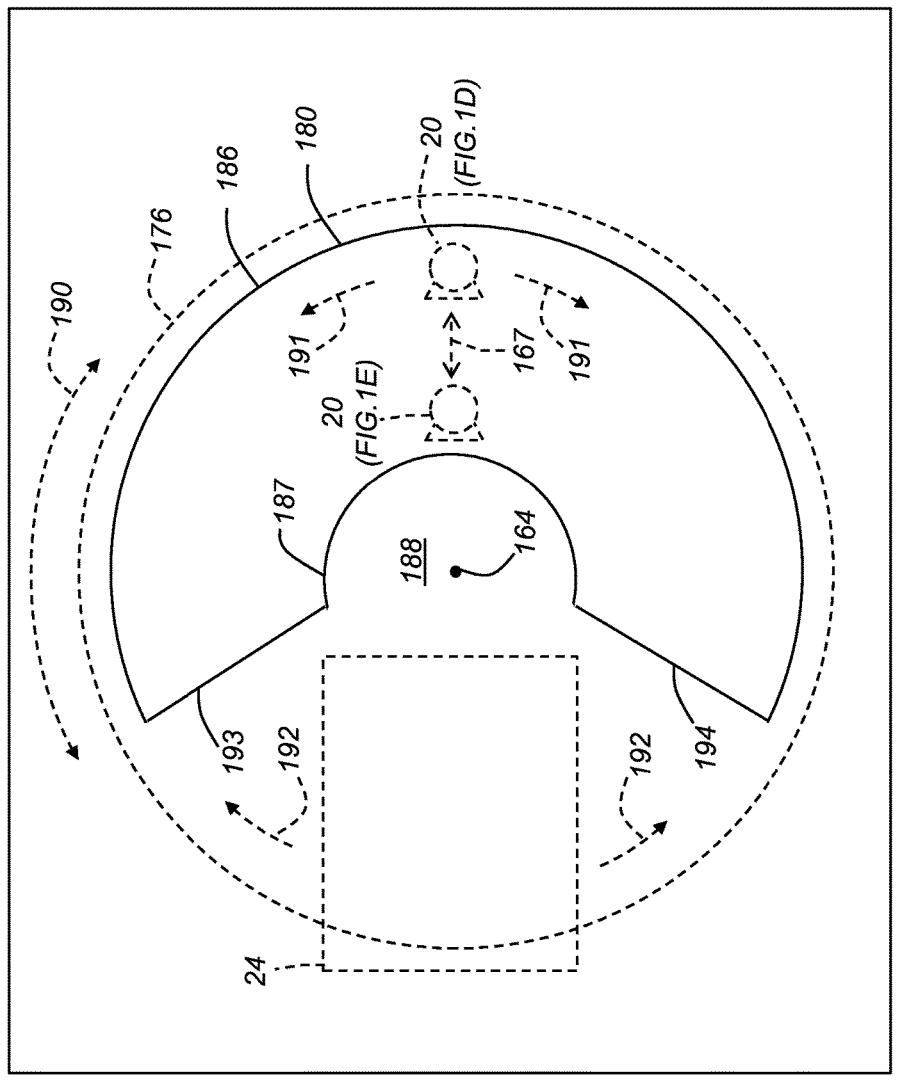
FIG. 1D is a diagram of a top view of a portion of the imaging system for animals of FIGS. 1B-C.

FIG. 1D is a partial top view of the embodiments of the imaging system 200 illustrated in FIGS. 1B-C. In one embodiment, the rigid arm 166 of FIGS. 1B-C may alternatively be embodied by a disc 176 upon which the rigid extensions 173 and 165 are attached and whereby the disc is rotated in one of the directions indicated by arrow 190 during an x-ray imaging scan. The housing 180 may enclose the source 20 and its rigid extension 165, whereby the source 20 may be propelled along a circular or curved source path indicated by arrows 191 between source path end points defined by end walls 193, 194, of the housing 180. As described herein the detector 24 moves simultaneously along a corresponding circular or curved detector path, indicated by arrows 192, below the top surface 104. The source 20 and detector 24 revolve about the central axis 164, as described herein. A portion of the animal, such as a foreleg or hind leg, to be imaged by the imaging system 200 may be positioned at or proximate the central axis 164. Alternatively, two or more limbs of the animal may be positioned proximate the central axis 164 for an imaging scan, for example, by having the animal stand in the open space 188 of the housing 180. The housing 180 may be said to have a C-shape whereby the open space 188 provides room for an animal to stand proximate the central axis 164 for imaging purposes. An exterior wall 186 of the housing 180 facing away from an animal positioned for scanning may be made of a radio opaque material to prevent x-ray scatter into the environment surrounding the imaging system 200. In one embodiment, the end walls 193, 194, are also made from a radio opaque material. An interior wall 187 of the housing 180 facing an animal positioned for scanning may be made of a radiolucent material to allow x-ray beam 163 to penetrate a portion of the animal to be imaged. In the embodiment illustrated in FIG. 1D, an arc of the source path 191 may extend greater than 180 degrees of a circular arc, as measured between its end points at end walls 193, 194 of the housing 180, whereby the arc of the corresponding detector path 192 may be substantially equivalent. In other embodiments, the housing and source path may be configured to enclose a source 20 and its source path 191 up to about 240 degrees to enable 3D imaging of the limb or limbs of an animal using an arc of 180 degrees plus the fan angle of the x-ray beam 163.

Figure 1E:
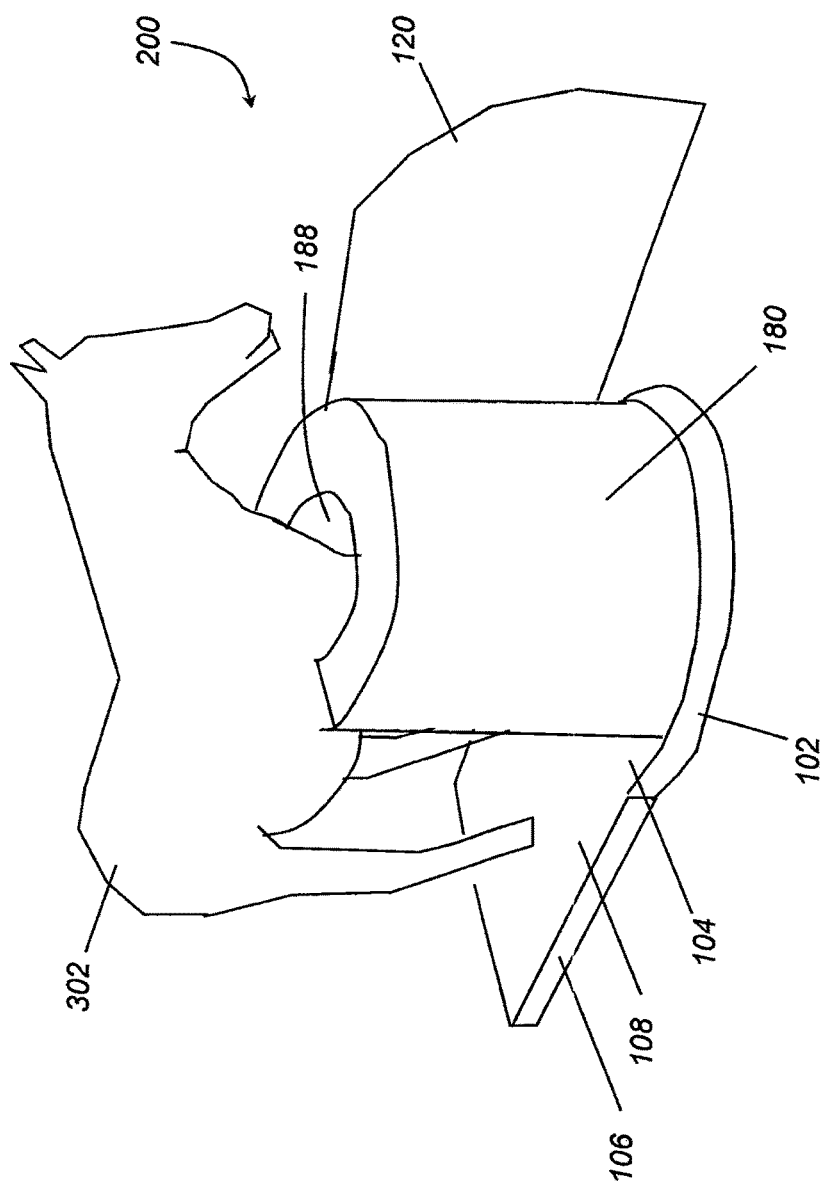
FIG. 1E is a perspective view of the exemplary imaging system for animals of FIGS. 1B-D having a subject animal guided into an imaging position.

FIG. 1E is a perspective view of the imaging system 200 embodiment of FIGS. 1B-C. An exemplary standing animal 302 may be guided into and be positioned within the open space 188 of the C-shaped housing 180 whereby one or both of its forelegs is positioned proximate the central axis 164 of the source and detector (not shown) for an x-ray imaging scan. As described herein, the source 20 is disposed with the housing 180 above the floor 104 while the associated detector 24 is disposed beneath the surface of the floor 104. The top surface 104 of the support base 102 may comprise of a material that is simultaneously rigid and radiologically translucent so that the detector 24 may receive the x-rays emitted by the source 20 and passing through a limb of the animal 302. Such a material may be a polycarbonate such as LEXAN. The motor 182 and rigid arm 166 assembly may be controlled using a threaded gear or other equivalent methods. The motorized bracket 175 may modify the position of the detector 24. The bracket 175, or bucky, may be attached to the rigid extension 173 that is configured to slide and keep the bottom of the detector 24 at a fixed height but allowing the detector 24 to slide parallel to the rigid arm 166. As the motorized bracket raises one end of the detector 24 along the vertical direction 168, the other end of the detector 26 may be moved toward the bracket 175 along the direction 169, in effect changing the angle of the detector 24, making it more vertical. Conversely, the vertical angle may also be reduced, as desired.

Figure 2:
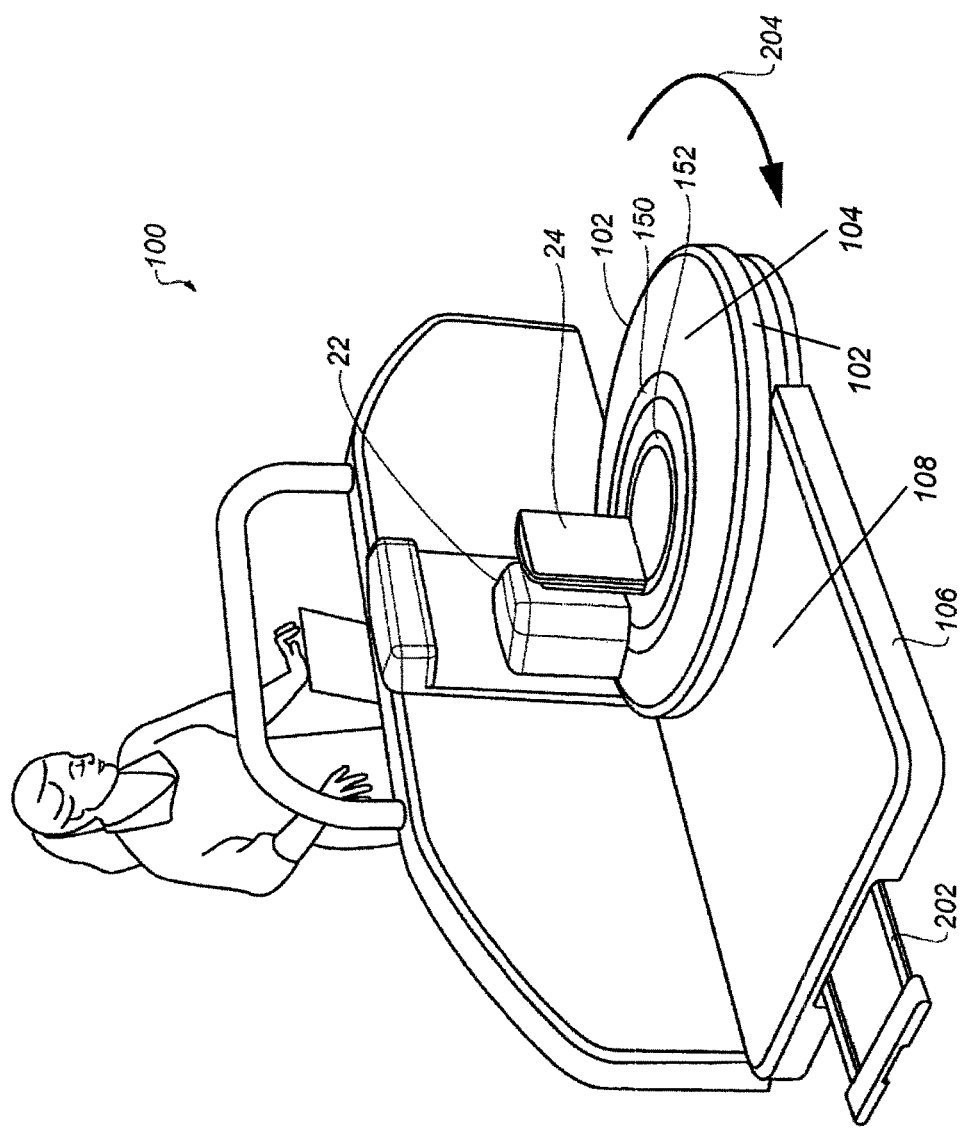
FIG. 2 is another perspective view of an embodiment of the exemplary imaging system for animals of FIG. 1A.

FIG. 2 illustrates an embodiment of the imaging system 100 whereby several features thereof may be incorporated into the imaging system 200 described herein. FIG. 2 illustrates an embodiment whereby another position of the moveable platform 106 with respect to the support base 102, which may be revolved along the direction indicated by arrow 204, and which position may be desirable depending on an orientation of the imaging location wherein the imaging system 100 may be installed to allow easier ingress and egress of an animal onto the imaging system 100. The platform 106 may be motorized and include casters along a bottom surface thereof for revolving it into the position shown. A handle 202 may be provided to manually revolve the platform 106 to selected positions around the support base 102. Although FIGS. 1A and 2 illustrate positions of the platform 106 at opposite terminal positions, the platform 106 may be secured at any position between these terminal positions. The detector 24 is shown in FIG. 2 revolved along the slot, or ring, 152 into a position adjacent the source 24 and opposite the position of the detector 24 as shown in FIG. 1A, which may be referred to herein as a neutral stop position, so that it does not impede comfortable movement of the animal onto the imaging system 100 prior to imaging exposures of the subject animal.

Figure 3:
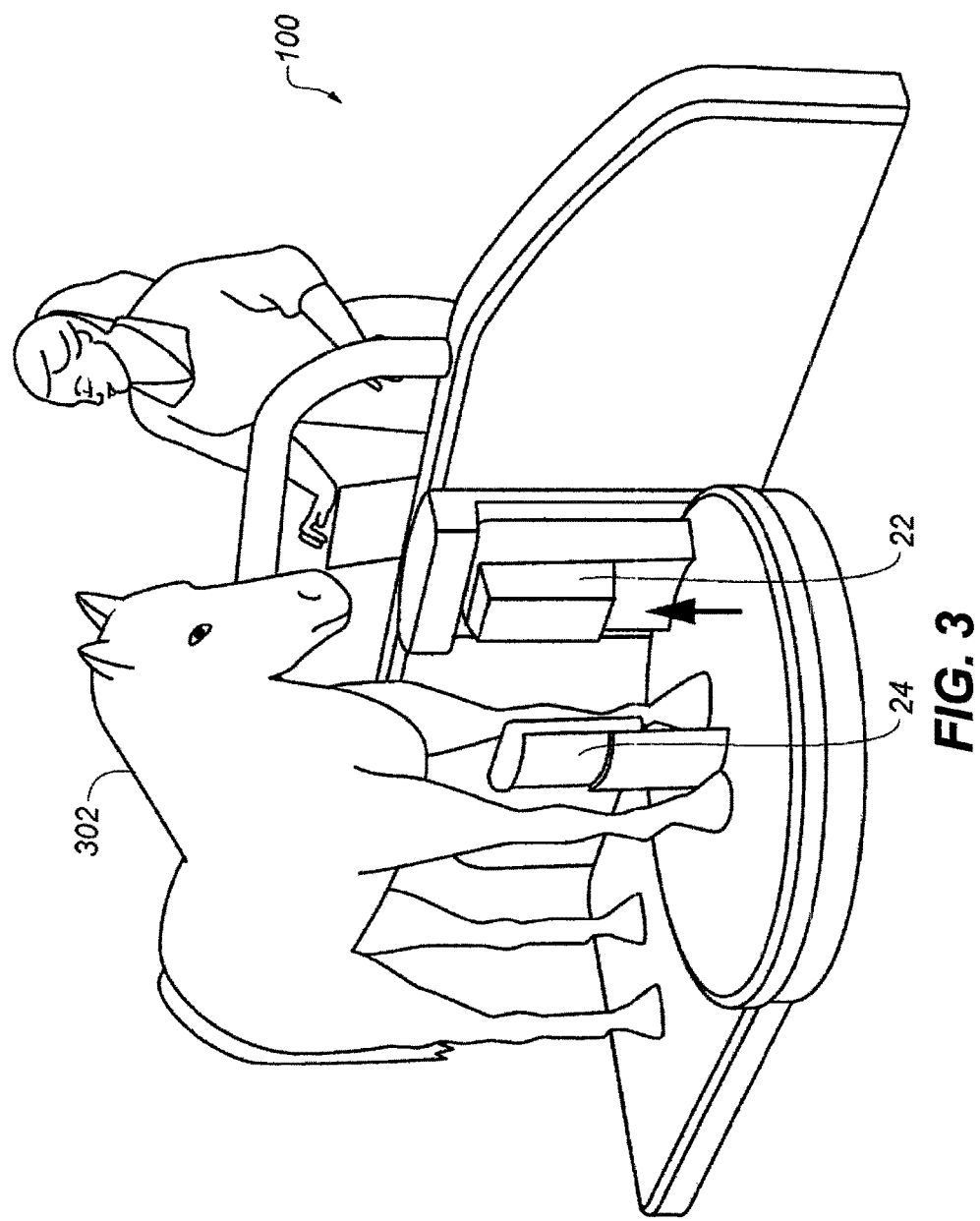
FIG. 3 is another perspective view of an embodiment of the exemplary imaging system for animals of FIG. 1A with a representation of a subject animal in position for imaging.

FIG. 3 illustrates an embodiment of the imaging system 100 whereby several features thereof may be incorporated into the imaging system 200 described herein. FIG. 3 illustrates imaging system 100 showing an exemplary subject animal 302, i.e. a horse, positioned for imaging by the source 20 and detector 24 of imaging system 100. As shown, the left foreleg of the subject animal 302 may be positioned between the source and detector for a single projection image exposure, or for a CBCT scan which may require activation of the orbital transport mechanism described herein for the source and detector, as the case may be. FIG. 3 also illustrates a feature of the source and detector which includes a mechanism for raising the source and detector in order to capture a radiographic exposure of the left foreleg of the horse 302 at a greater height than would be captured if the source and detector remain at their lowest position. This feature of the source and detector allows movement to any position between a lowest unraised position of the source and detector and a highest raised position thereof. Such movement may be implemented by a built-in motorized control or may be implemented manually such as by a detente mechanism for the source and detector having several stops between the raised and unraised positions. According to one embodiment, an adjustable manual motor control or a foot pedal motor control may include a fine-tuning capability for the height adjustment of the source and detector. In one embodiment, a single actuation of the control may automatically adjust the height of the source, the detector, or both, by a programmed amount (e.g., 1 cm). The source housing 22 20 may include a collimator for limiting an emitted radiation beam width of the source and changing or scaling a beam aspect ratio. One or more beam redirection devices may be employed to extend the angular range of the radiation source 20. Raising the source and detector does not interfere with operation of the orbital transport mechanism which may be activated for image capture at any raised position of the source and detector, or which may be simultaneously activated with the raising or lowering such as for a helical scan imaging sequence.

Figure 4:
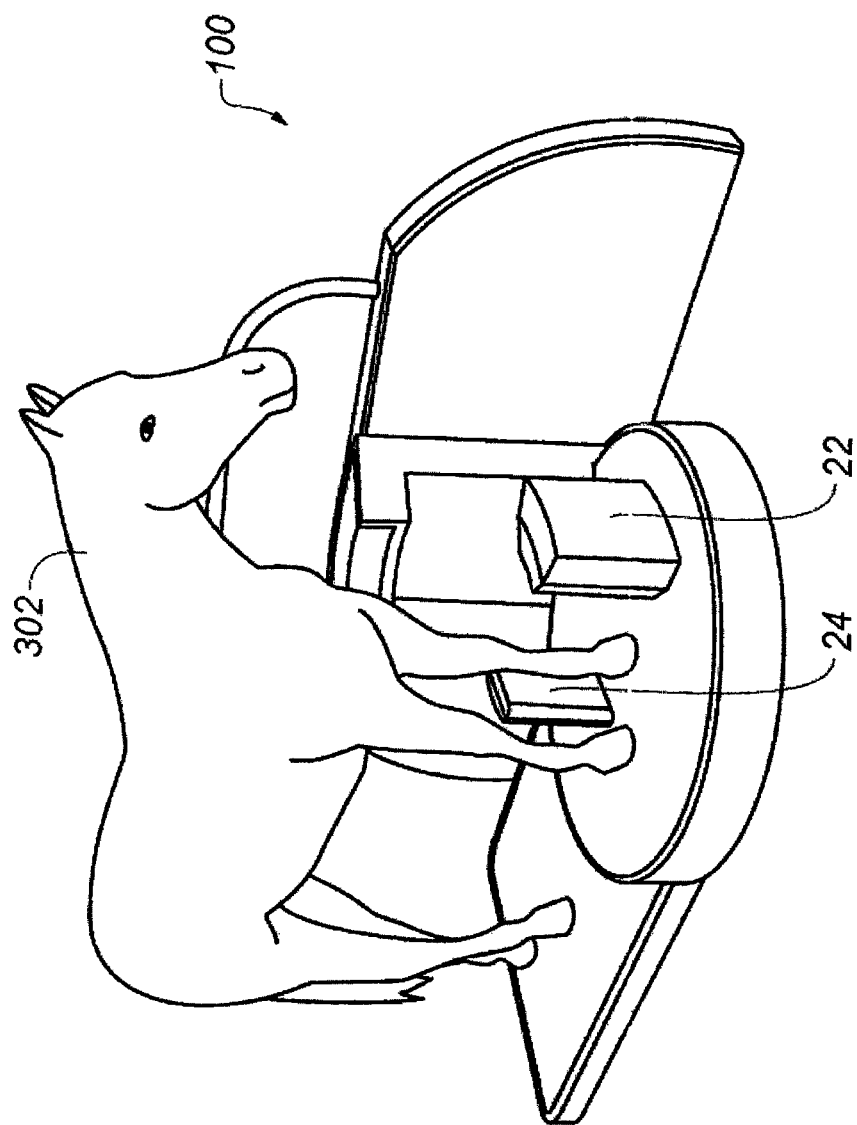
FIG. 4 is a perspective views of an embodiment of the exemplary imaging system for animals of FIG. 1A with a representation of a subject animal in position for imaging.

FIG. 4 illustrates an embodiment of the imaging system 100 whereby several features thereof may be incorporated into the imaging system 200 described herein. FIG. 4 illustrates imaging system 100 showing the exemplary subject animal 302 being imaged, whereby the source 20 and detector 24 of imaging system 100 are being revolved during a CBCT scanning sequence. As shown, the left foreleg of the subject animal 302 may be being imaged as the source and detector are revolved about that limb. The left foreleg of the horse 302 may be positioned in the axis of revolution of the source and detector and remains directly between the source and detector during the imaging sequence. As shown in FIG. 4, the source and detector may also be used for a single radiographic projection image exposure in the position shown, as desired.

Figure 5:
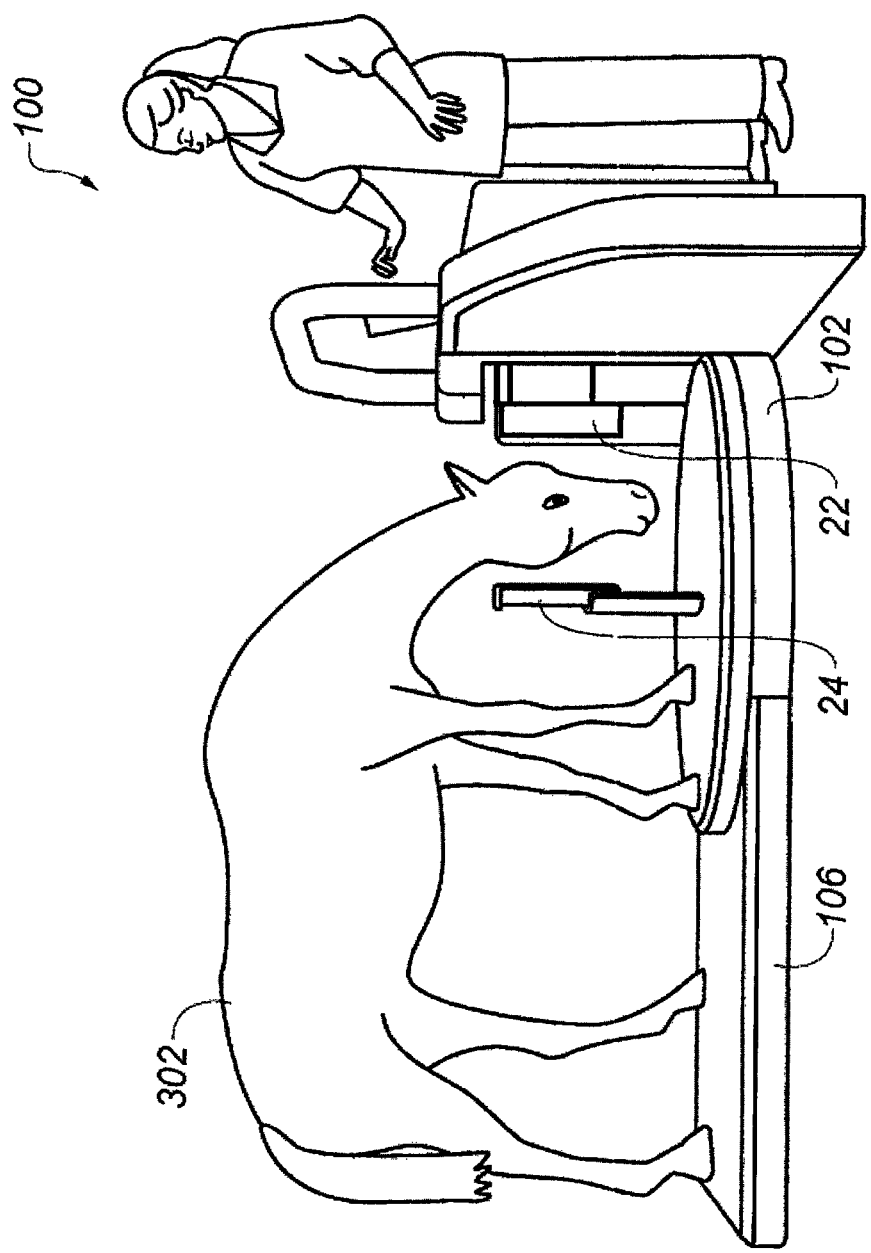
FIG. 5 is another perspective view of an embodiment of the exemplary imaging system for animals of FIG. 1A with a representation of a subject animal in position for imaging.

FIG. 5 illustrates an embodiment of the imaging system 100 whereby several features thereof may be incorporated into the imaging system 200 described herein. With respect to FIG. 5, the imaging system 100 is shown whereby the platform 106 has been moved to an intermediate position between the terminal positions with respect to the support base 102. This position of the platform 106 may be used for imaging the head of a subject animal, as shown, by placing its head between the source 20 and detector 24. The source and detector may be configured, such as increasing a space between them, to allow the animal to move its head to a lowered position therebetween. The top surface 104 of the support base 102 may be modified to include a recess in order to make room for the subject animals' snout, for example. In one embodiment, the source and detector may be mounted on a gimbal (e.g., universal joint) to be revolved, or maintained in a selected stationary position, for imaging the head of an animal. In one embodiment, the source and detector may be configured, e.g. programmed, to rotate up to about 90 degrees for imaging an animal's head. A leaning bar or surface against which the subject animal may apply its head with some amount of pressure helps to stabilize the head position during exposure. In one embodiment, a scan volume of the CBCT system may be increased (e.g., wider, longer) for head imaging. For hind leg imaging, handling of the subject animal for positioning may differ from front leg imaging. It may be useful to back the animal toward the source and detector components or to cross past these components and stop or restrain the subject at a given position. There may be some image processing differences based on particular aspects of animal imaging. One or more projection images may be rejected from the sequence due to excessive motion, for example. The range of imaging angles may be varied for different subjects, such as according to positions at which the animal remained still.

Although one platform 106, has been illustrated and described as a complementary structure for support base 102, more than one connecting platform may be coupled to the support base 102 to extend the top surface 104 thereof in order to support larger animals during an imaging sequence. As described above, the connecting platform may be rotated to a suitable angle about the support base 102, depending on the desired orientation of the animal for a specific radiographic exam. In one embodiment, the connecting platform 106 may include a ramp portion attached to support base 102 for ease of transporting a subject animal onto the imaging systems 100, 200. The platform 106 may alternately include a height adjustment mechanism to lift or lower the platform as well as the subject animal. Multiple attachable platforms may be provided to be added or removed from the support base 102, as needed. It may be advantageous to have the subject's front and hind legs on the same or a different level (height), as desired, for a particular imaging sequence.

Although the present invention may be not limited to a particular construction of the source 20, it may include a linear or a two-dimensional ("2D") array of radiation sources, such as carbon nano-tube (CNT) sources. In one embodiment, at least one of multiple sources may be removably (e.g., re-attachable) installed and, when detached, the remaining sources may be coordinated with the detector for projection radiography. Multiple radiation sources may be included to be separately energized, or energized as a group. The housing 22 of the radiation source 20 may provide shielding from the x-ray tube or other radiation emitter and related equipment. The source housing 22 may be manually removable and attachable from the base support 102 and, when replaced, rotates together with the source. The radiation source housing 22 may have a knock-down or break-away feature, so that the housing and its source may be movable from an imaging position, in the event of kicking or other sudden, unpredictable responses of the subject animal. This provides a measure of damage protection for the source.

The detector 24 may include a digital radiography ("DR") detector that acquires images at a rate that may be commensurate with a corresponding imaging position of the source. The detector may comprise a digital flat panel detector having a generally planar, rigid, rectangular shape. The detector 24 may be configured to transmit acquired radiographic image data to the processing system 130 over a wired or a wireless communication link. According to embodiments of the present invention, detectors of different sizes may be usable in the detector housing. This enables use of detectors of different sizes or capabilities suitable for specific imaging applications. The detector may be removable from the support base 102 or from the bracket, or bucky, 175.

The processing system 130 may control component operation of the imaging systems 100, 200 for setup, exposure control, scanning, including control of platform transport mechanisms, image data acquisition, image processing, and presenting image data on the display 132. Image processing functions may be partially or mainly performed by a processor in the detector, prior to transmission of the acquired image data to the processing system 130. An operator/user interface on the display 132 may provide utilities for entry of operator commands. In one embodiment, multiple displays may be provided to allow animal handlers or veterinary personnel to view instructions for setup as well as results, such as with images displayed as acquired. Images may be refreshed at a lower rate than the acquisition rate, but sufficient for determining whether or not the appropriate anatomy of the subject animal is being imaged. The operator interface may be provided on a movable, free-standing, processing system console that includes a display 132. Wired or wireless connection of the console to the detector and source may be available. Cabling may extend into the support base 102 for interconnection of the detector and source components to the processing system 130 as well as for transmission of image signals, power, and data to control the detector and source orbital transport apparatus. According to an alternate embodiment, cables may be tethered to one or more components mounted on or internal to the support base 102 from above or from alongside the imaging system.

The orbital transport apparatus may be configured to allow the source 20 to move independently of the detector 24 during setup of the imaging systems 100, 200, such as during positioning of the subject animal for imaging. The detector portion of the orbital transport apparatus revolves the detector about the subject animal extremity to be imaged. In one embodiment, the detector path may be configured to travel around at least a portion of the scan volume. In one embodiment, the source revolves along a circular path having a diameter greater than the detector's path. A center of the source and detector paths may coincide with a center of the support base 102 or they may be offset. As with the source, the detector may generally orbit about common central axis so that its radius has a fixed value for any CBCT imaging sequence.

Embodiments of the extremity imaging systems 100, 200, may include portable configurations to allow ready transport to on-site imaging locations such as at a stable, veterinary clinic, or other imaging site. A trailer-mounted version of the imaging systems 100, 200, may be built onto a trailer that may be driven or hauled from site to site. A ramp or other device may be used to lead the subject animal onto the trailer for an imaging exam. A depression or well may be provided in the trailer. The surface or floor of the trailer bed may provide the functions of the support base or floor as described herein. For the trailer-mounted version, sides of the trailer may lift out or be hinged to increase the platform area available. The horse or other animal may climb up onto the trailer. A number of supporting components such as walls, railing, shields, lead aprons, and the like may be configured on and around the support base in a mobile scanning apparatus. Vent holes and other features may be provided in the trailer base for facilitating removal of solid and liquid waste, water, and cleaning fluids. Embodiments of the imaging systems 100, 200, may be transported on a trailer and unloaded from the trailer for set-up at a remote imaging site.

According to an embodiment of the present invention, the subject animal may be positioned such that its leg, or other anatomical region to be imaged, may be placed in a target location, such as proximate the central axis 164. After positioning the subject animal, the source and detector may be then moved into an imaging start position and, over a range of angles, controllably orbit the leg or other anatomy to be imaged. A scanning sequence may be executed by moving the source and detector in either clockwise or counter-clockwise motion about the subject animal's anatomy. Helical or spiral imaging patterns may also be provided, wherein the source and detector are activated to revolve about the subject animal's extremity while simultaneously raising, and/or lowering, the source and detector as described herein. A helical scan may be used, for example, for long-length imaging of a limb of the subject animal. In one embodiment, dual scans at different height positions of the source and detector may be performed back to back, and then projection images or reconstructed 3D volume images may be combined together such as by digital stitching. According to an embodiment, the operator may designate, i.e., program, an appropriate starting and ending angle for a particular scan sequence. Thus, for example, where it may be challenging to position an animal properly, the scan operation of the system may be adapted to compensate to generate the desired radiographic image. In one embodiment, for example, the detector imaging path may cover 360 degrees so that a particular exposure arc (e.g., 180 degrees plus cone angle) may be selected anywhere within the 360 degree range. It may be desirable to obtain images over a range of angles where the subject animal may be most stably positioned in a non-standard stance. The source and detector may be programmed to start imaging at a particular angle that may be most favorable, given these conditions. This may be a particular advantage for tomography and other imaging modes.

In a method of operating the imaging systems 100, 200, an exemplary sequence of method steps will now be described.

Figure 7:
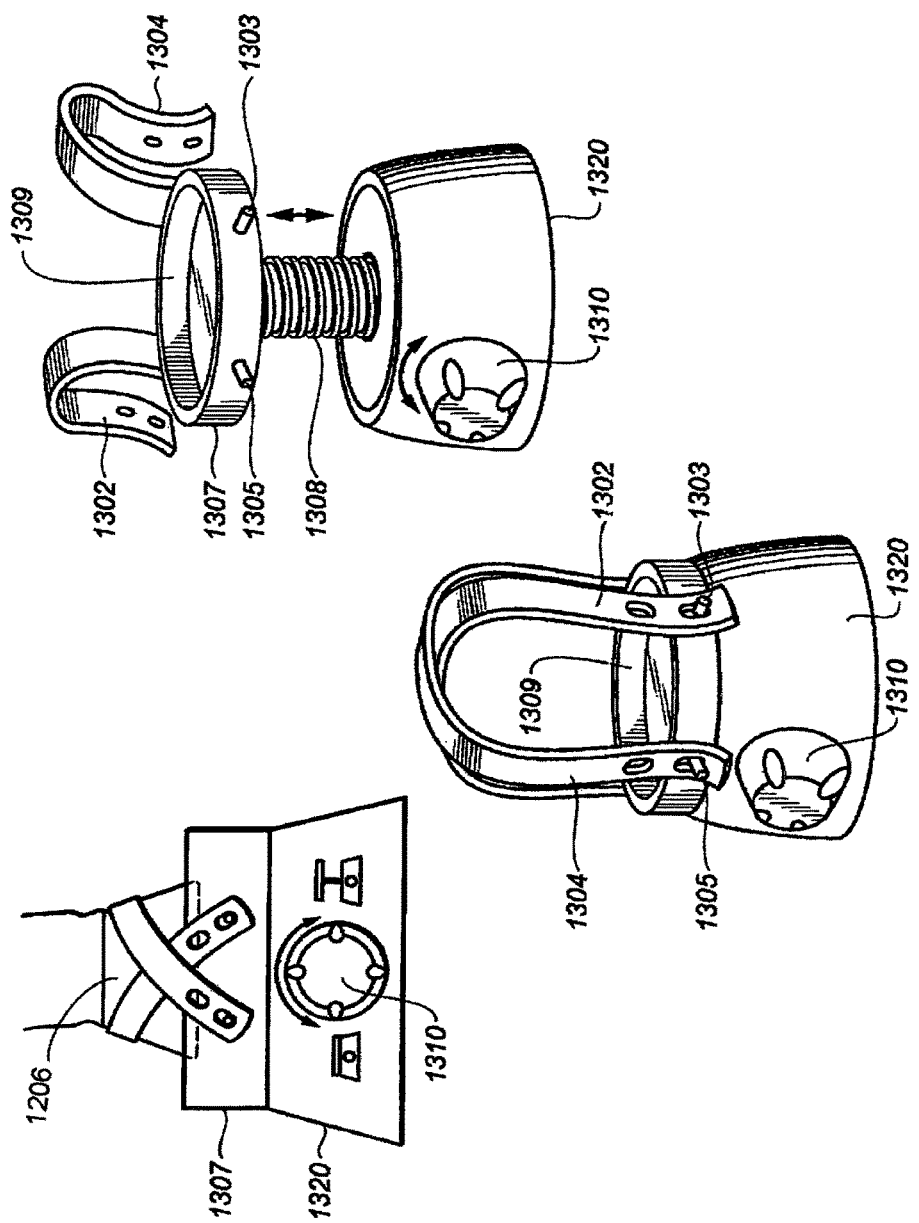
FIG. 7 contains views of an embodiment of an exemplary foot restraint useable with the pedestal of FIG. 6A.

1. Lead and position the subject animal for image acquisition. Various features may be provided to help guide the horse or other subject animal into position. Either or both the detector housing and the radiation source housing in the imaging system 100 (not required for imaging system 200 embodiment) may be moved to a neutral position while the horse or other animal is guided into place.
2. Alternatively place protective shields, aprons, curtains, or other coverings into place to hide or disguise the imaging components from the animal, typically for imaging system 100 embodiment.
3. Position the anatomical portion of the animal (e.g., an extremity) to be imaged at or proximate the central rotational axis between the source and the detector, or move the source and detector into position about the extremity of the animal. This step may involve using various devices such as bars, a tunnel, barriers to assist in guiding and positioning the animal, or other components, such as illustrated in FIGS. 6A-7, where these devices constrain movement of the subject extremity. In one embodiment, a scan gate may be placed between the horse's imaged legs to (i) ensure there is existing room for the detector and/or (ii) reduce the likelihood that the detector contacts the horse's imaged leg during the scan or image exposure sequence.
4. Execute the image exposure sequence, as described herein, by activating the source and detector.
5. Restore the source and detector to interim neutral positions, if necessary, after removing the scan gate, if any.
6. Guide the animal away from the imaging system.

Additional features may be provided for making the subject animal more secure and less likely to be frightened and kick or otherwise become too agitated to remain still during imaging. These may include visual stimuli or blinds; music, white noise or other audible stimulus; fans or other external devices for moving air past the animal; smells; liquids; heat, cold, or other stimuli. In other embodiments, the sound, white noise or music may be selected to begin at a first level (e.g., low or inaudible to the horse) and end at a second level sufficient to cover or be louder than the CBCT imaging system (e.g., to mask moving sounds of the source/detector and noise caused by the radiation source/generator). In one embodiment, an intermediate level of noise may be used to cover the general operating sound of the CBCT apparatus when not imaging. For any stimulus, variation in strength or intensity may be used to provide a more natural distraction for the animal, such as increasing or changing a sound volume or fan speed, for example.

With respect to FIGS. 6A-7, in particular, FIGS. 6A-C, imaging a hoof 1206 or lower leg portions of a subject animal may be improved using a pedestal 1204 or other device to position the hoof 1206. The pedestal 1204 may be formed to include an angled support 1222 to suit the shape of the hoof. A hydraulic lift 1208, worm gear, or lead screw, for example, may be connected to a bottom of the pedestal 1204 and raised to elevate the pedestal 1204 to a desired imaging position. The pedestal 1204 may be located in the support base 102 between the source and detector in the embodiments described hereinabove, or it may be located in the shortened support base 902 between the radiation source 1202 and the DR detector 1203, for example. In one embodiment, the hoof may be placed upon, or secured to, a pedestal 1204, which, in turn, may be coupled to the support base 902. A control at the base of the pedestal allows the technician to raise or lower the pedestal as needed.

With respect to FIGS. 6A-7, a clamp 1402, straps 1302, 1304, or other device may alternately be used to constrain a hoof of an animal standing within the C-shaped housing 180. The hoof may be placed in a pedestal 1307 having a recessed cavity 1309 to receive the hoof Straps 1302, 1304, having holes therethrough may be wrapped around the hoof and affixed to securing pins 1303, 1305, respectively. A height of the pedestal 1307 may be adjusted using a screw 1308 attached to the bottom 1320 of the pedestal 1307 or by turning a knob 1310 configured to activate a mechanism in a base portion 1320 of the pedestal 1307. Where the scanning components may be moved to below the top surface of the support base 102, 902, the hoof may be placed directly on the top surface. In one embodiment, the detector may be positioned below the top surface 104 of the support base 102 to orient the detector lower edge below the imaged hoof. In one embodiment, a surface configuration of the support base 102, 902 may be made from X-ray transmissive material to allow imaging by the detector when recessed into the support base 102, 902.

Certain exemplary imaging systems 100, 200, embodiments may provide the platform and support base having at least two heights, a first lower height for standard imaging and a second higher height for hoof imaging. For the second height, intermediate height additional platform may be used to allow the horse to reach the second higher height, which may be higher than a horse may step. Alternatively, a ramped additional platform may be used to get the horse to the second higher height. In one embodiment, at the second higher height configuration, the platform and support base outside the source path may be at the second higher height, but the source, detector and an inner region remain at the first lower height. In one exemplary second higher height configuration, an area inside the source path may be filled with: (i) a first radiation transmissive ring coupled to rotate with the source, (ii) a second intermediate radiation transmissive ring coupled to rotate with the detector, and (iii) an inner radiation transmissive region to support the hoof. In an alternative embodiment for the source, the source may be configured to move/extend to a height above the detector, even with the inner region or above the inner region, and may be configured to shift to one or more angled orientations to improve alignment with the detector (e.g., through the inner region). The detector and source may be both elevated for knee and hock imaging, as shown in FIG. 3. Height may be manually adjustable or adjustable using a motor or other actuator in detector housing or radiation source housing.

In the imaging systems described herein, movement sensing may be optionally provided. This may be done in a number of ways. An optical camera may be used, according to an embodiment of the present invention, for determining whether or not movement of the animal during or before imaging may be excessive. Weight sensors, such as sensors embedded in the support base may be used to indicate weight-bearing condition for the subject extremity to be imaged and to indicate movement of the subject.

One or more platforms may be cooperatively coupled with the support base to support the animal. The platforms may be repositioned as needed according to the desired orientation of the subject for imaging. The platforms may be also covered with a heavy duty mat surface to help prevent slipping and provide a more comfortable surface. To allow ease of movement, platforms may be on casters, such as on spring-loaded, heavy duty casters. Walls may be provided with and without side panels. Walls may be provided with one or more access openings to allow access to source, detector, or the subject. An opening may slide or be hinged to allow access. The walls may be installed or positioned/re-positioned before or after the subject animal may be in position for the imaging session. Walls may be directly coupled to the support base. Walls may alternately be coupled to the control console.

Configurable guide rails may be provided to help in guidance and support, to provide structures for bindings, and to constrain movement of the subject. Guide rails may be removable and fitted into holes in the wall and other structures as needed. Fasteners may be provided to secure guide bars in place, with or without tools. Fasteners may be integral to the guide bars, such as captive bolts or clasps. Various types of restraint devices may be fitted around the animal, including foam inserts, air splints, bits, cross bars, or bindings, for example. This may include a bar that may be set in front of or between front or rear legs of the subject. A headrest may also be provided, allowing the animal to push against a surface to stabilize position or posture. A bar or other feature for resting against the chest, or receiving pressure from the subject along the chest, may also be useful.

Various types of hard or soft coverings may be provided for masking off one or more components of the extremity imaging scanning apparatus from the subject animal's field of view. Some amount of covering tends to alleviate animal anxiety from observing moving parts, for example. Coverings may serve a dual purpose, such as providing some measure of radiation shielding, for example. A chest rest bar may be provided separately or with the covering/apron/ radiation shield. The chest rest bar may provide orientation for the animal, support for the horse to lean against, physical protection for a human handler (e.g., when used to guide or control the animal). In one embodiment, a structure may be configured to engage the chest of the horse with sufficient force for the horse to push against, extend horizontally (e.g., until outside the source path), drop vertically to be coupled to the support base. In one configuration, the drop to the support base may be angled, become wider or separate into divided sections (e.g., mounts or legs), implemented in stages or using a curved molded shape. Preferably the structure may be (a) sufficiently sized/wide/tall to hide the detector path and/or the source path from the animal, (b) to orient the animal, (c) sufficiently rigid/resistant to allow the animal to lean against, (d) sized to allow a handler to stand behind but in position to access the horse, (e) configured to provide radiation protection for a handler when equipped with a X-ray or radiation shield (e.g., apron), which may be integrated or attachable. In one embodiment, the structure may be attached to the support base, the platform or other part of the CBCT apparatus, or to the floor, wall or the like. In one embodiment, the structure may be configured to partially or fully encircle the horse's head/neck. In one embodiment, the structure may extend vertically to provide sufficient radiation protection to the human handler. In one embodiment, the structure may include a display or the like to provide information to the human handler such as an in-progress indicator that shows the time expended/remaining in an exposure. In one embodiment, the display on the structure may be a duplicate console to allow the technician to operate the CBCT apparatus from adjacent the structure. Other types of apron and curtain or draping may be used, draped over various parts of the animal and over equipment components.

Radiation shielding may be provided behind the detector and by a number of system components. Shielding may be integral to transport apparatus, walls, coverings, guide bars, tunnels, and other features. Additional shields may be designed and placed about or against the subject during imaging. Aprons, headgear, chest and arm protectors, gloves, boots, leggings, and protective pads may be provided for animal handlers and technicians who may need to support the animal during exposure. Interlocks may be provided to ascertain that protective gear has been donned by attending personnel. Interlocks may also be provided to verify that particular shielding structures may be in place. For example, an interlock may be provided to check that the operator console is behind the wall relative to the radiation source. The extremity imaging apparatus may be designed to allow various cleaning solutions to be used without damage to the equipment and allows hose cleaning. Disassembly of parts allows access for wiping down components and cleaning fittings.

The radiation source and detector may be temporarily disengaged from the support base to allow cleaning. Surfaces of the extremity imaging apparatus may be washable to allow regular cleaning. Various types of plastics or metals such as stainless steel may be used. According to an embodiment of the present invention, various components of the extremity imaging apparatus may be designed to fold down or break away when kicked. Magnets or other devices may be used to maintain components in position while allowing the needed amount of holding force/yield capability. The operator interface at the processor display console lists available exam types. Some variables may be allowed for specific exams or modalities. Among variables that may be changed by the operator may be starting and ending angles for orbit motion of source and detector. According to an embodiment, the operator display shows the relative angle of the source and detector when positioned in the track or slot of the support base. The display shows results with operator or actuator movement of the source or detector to a different angle.

A number of default positions may be set up according to the operator selection of an exam type. Initial positioning of imaging components places them at these default positions. Operator instructions may be provided for options on positioning and constraining the animal. Based on the exam type, the operator instructions may show the options available for the exam. The operator may set energy levels (kVp) and make other settings and adjustments to exposure-related parameters. The angular range and resolution may be set. The user interface allows exam initiation and termination. A trigger may be provided, removable from the operator console such as on a tether, for initiation of exposure. The operator interface screen displays results of 2-D projection images as they are captured, as well as the 3-D reconstructed image that may be generated. Various parameters related to the subject may be displayed and monitored during imaging, including heart rate, muscle tension, and other parameters. A touchscreen interface may be provided. Alternately, an optional keyboard and mouse may be used for command entry. The operator display screen may show a layout of the imaging apparatus with the area that may be irradiated during movement of the radiation source highlighted. This helps to indicate where shielding may be provided and where personnel access should be restricted to only those wearing protective gear. The detector and radiation source may be moved out of imaging position for leading the animal into the apparatus or exiting the imaging apparatus. Detents or other guides may be provided in order to obtain precise alignment. An operator interface command also permits a dry-run, allowing handler and other personnel to observe animal response, such as to movement of imaging devices. A calibration sequence may be provided for periodic recalibration of the detector. According to an embodiment of the present invention, at least one dry-run cycle may be provided, during which the source and detector orbit the subject, but without exposure. This enables the setup to be quickly evaluated and allows observation of the subject's response to component movement.

Consistent with at least one embodiment, exemplary methods/apparatus may use a computer program with stored instructions that perform on image data that may be accessed from an electronic memory. As may be appreciated by those skilled in the image processing arts, a computer program of an embodiment herein may be utilized by a suitable, general-purpose computer system, such as a personal computer or workstation. However, many other types of computer systems may be used to execute the computer program of described exemplary embodiments, including an arrangement of networked processors, for example.

The computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that may be connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, may refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that may be used as a temporary buffer or workspace by a microprocessor or other control logic processor device. Display data, for example, may be typically stored in a temporary storage buffer that may be directly associated with a display device and may be periodically refreshed as needed in order to provide displayed data. This temporary storage buffer may also be considered to be a memory, as the term may be used in the present disclosure. Memory may be also used as the data workspace for executing and storing intermediate and final results of calculations and other processing. Computer-accessible memory may be volatile, non-volatile, or a hybrid combination of volatile and non-volatile types.

It will be understood that computer program products for exemplary embodiments herein may make use of various image manipulation algorithms and processes that may be well known. It will be further understood that exemplary computer program product embodiments herein may embody algorithms and processes not specifically shown or described herein that may be useful for implementation. Such algorithms and processes may include conventional utilities that may be within the ordinary skill of the image processing arts. Additional aspects of such algorithms and systems, and hardware and/or software for producing and otherwise processing the images or co-operating with the computer program product of the application, may be not specifically shown or described herein and may be selected from such algorithms, systems, hardware, components and elements known in the art.

It should be noted that while the present description and examples are primarily directed to radiographic medical imaging of an animal or other subject, embodiments of apparatus and methods of the present application may also be applied to other radiographic imaging applications. This includes applications such as non-destructive testing (NDT), for which radiographic images may be obtained and provided with different processing treatments in order to accentuate different features of the imaged subject.

Although sometimes described herein with respect to CBCT digital radiography systems, embodiments of the application are not intended to be so limited. For example, other DR imaging system such as dental DR imaging systems, mobile DR imaging systems or room-based DR imaging systems may utilize method and apparatus embodiments according to the application. As described herein, an exemplary planar panel DR detector/imager may be capable of both single shot (radiographic) and continuous (fluoroscopic) image acquisition. Further, a fan beam CT DR imaging system may be used.

Exemplary DR detectors may be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation. Exemplary embodiments according to the application may include various features described herein (individually or in combination).

While the invention has been illustrated with respect to one or more implementations, alterations and/or modifications may be made to the illustrated examples without departing from the spirit and scope of the appended claims. In addition, while a particular feature of the invention may have been disclosed with respect to only one of several implementations/embodiments, such feature may be combined with one or more other features of the other implementations/embodiments as may be desired and advantageous for any given or particular function. The term "at least one of" may be used to mean one or more of the listed items may be selected. The term "about" indicates that the value listed may be somewhat altered, as long as the alteration does not result in nonconformance of the process or structure to the illustrated embodiment. Finally, "exemplary" indicates the description may be used as an example, rather than implying that it may be an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An apparatus for radiographic imaging of an animal, the apparatus comprising:
   a floor to support an animal standing on its legs;
   a moveable x-ray source disposed above a surface of the floor within a source housing and mechanically attached to a rotation mechanism; and
   a digital radiographic detector disposed below the surface of the floor and mechanically attached to the rotation mechanism, wherein the source housing remains stationary, and wherein the x-ray source and the detector are configured to revolve around at least one extremity of the animal to capture at least one radiographic image thereof.

2. The apparatus of claim 1, wherein the source and the detector are configured to both revolve about said at least one extremity of the animal while capturing a plurality of radiographic images of said one extremity of the animal, said one extremity of the animal comprises a head, a foreleg, or rear leg, and wherein a radius of a revolution path of the source is greater than a radius of a revolution path of the detector.

3. The apparatus of claim 2, wherein the source and the detector are configured to both revolve about said one extremity of the animal by a motor control that is programmed with a start position where the source and the detector begin revolving about said one extremity of the animal and a stop position where the source and detector stop revolving about said one extremity of the animal.

4. The apparatus of claim 3, wherein at least one of the source and the detector include a mechanism for increasing and decreasing the radius of its revolution path, the mechanism allowing at least one of the source and the detector to be moved further or closer to a central axis of the revolution path.

5. The apparatus of claim 4, further comprising an orbital transport mechanism below the floor, the detector is attached to the orbital transport mechanism, and wherein the orbital transport mechanism moves the detector along a detector path shaped as an arc of a circle equal to or greater than about 180 degrees.

6. The apparatus of claim 5, further comprising a mechanism for raising and lowering the x-ray source to different position above the floor.

7. The apparatus of claim 6, wherein the apparatus is configured such that the raising and lowering are performed simultaneously with revolving the source to perform a helical scan of the at least one of the limbs of the animal.

8. The apparatus of claim 7, further comprising a platform attached to the floor, wherein the platform is moveable about the floor to support the animal standing on the floor and on the platform, and to facilitate positioning of the animal relative to the source and detector for imaging different anatomical regions of the animal.

9. The apparatus of claim 8, wherein a height of the housing extends above the top surface of the floor between a height of about a knee of a horse positioned on the floor to a height of about a shoulder of the horse.

10. The apparatus of claim 9, wherein the housing is a substantially rigid housing having a hollow interior allowing movement therein of the source, and wherein the housing comprises a curved shape extending from a position in front of the horse and outward beyond sides of the horse to terminal positions on both sides of the horse between the front and hind legs thereof.

11. The apparatus of claim 10, wherein the platform is sized such that one or more extremity of the animal is supported by the platform and remaining legs of the animal are not supported by the platform.

12. The apparatus of claim 11, wherein the apparatus comprises a hardwired communication link to a processing system for controlling an imaging sequence of the at least one extremity of the animal and for receiving digital image data from the detector generated by the imaging sequence.

13. The apparatus of claim 12, further comprising a mechanism for lowering the source and the detector below the top surface of the floor through slots in the top surface of the floor.

14. An apparatus for radiographic imaging of a target, the apparatus comprising:
    a support structure to support the target, the support structure having a top side configured to support the target and a bottom side opposite the top side;
    an x-ray source above the top side of the support structure; and
    a digital radiographic detector below the bottom side of the support structure,
    wherein the x-ray source is aimed at the detector to emit x-rays through the support structure toward the detector throughout a radiographic imaging scan of the target, the x-ray source and the digital radiographic detector are mechanically connected to a mechanism configured to revolve the source and the detector greater than 180 degrees about an imaging axis to perform the radiographic imaging scan of the target, and wherein the x-ray source remains above the top side of the support structure aimed at the detector throughout the radiographic imaging scan of the target and the digital radiographic detector remains below the bottom side of the support structure throughout the radiographic imaging scan of the target.

15. The apparatus of claim 14, wherein at least a portion of the support structure is positioned parallel to a horizontal plane, and wherein the target is a portion of an animal standing on the support structure.

16. The apparatus of claim 15, wherein the x-ray source is disposed inside a curved housing attached to the top side of the support structure throughout the radiographic imaging scan of the target, and wherein the curved housing is configured to partially surround the target.

17. The apparatus of claim 15, wherein the imaging axis is substantially perpendicular to the top surface of the support structure and wherein the target is positioned proximate to or intersecting the imaging axis.

18. The apparatus of claim 17, wherein the source and the detector are configured to both revolve about the target while the detector captures a plurality of radiographic images of the target.

19. The apparatus of claim 18, wherein at least one of the source and the detector include a mechanism for increasing and decreasing its distance from the support structure.

20. The apparatus of claim 19, further comprising an orbital transport mechanism below the support structure, wherein the source and the detector are attached to the orbital transport mechanism, and wherein the orbital transport mechanism is configured to revolve the source and the detector about the imaging axis.

* * * * *